(12) United States Patent
Singh et al.

(10) Patent No.: US 9,090,546 B1
(45) Date of Patent: Jul. 28, 2015

(54) FLUORONATION OF ALPHA-HALOALKYL KETONES

(71) Applicants: Rajendra P. Singh, Broomfield, CO (US); Jerry Lynn Martin, Superior, CO (US)

(72) Inventors: Rajendra P. Singh, Broomfield, CO (US); Jerry Lynn Martin, Superior, CO (US)

(73) Assignee: CoorsTek FluoroChemicals, Inc., Arvada, CO (US)

( * ) Notice: Subject to any disclaimer, the term of this patent is extended or adjusted under 35 U.S.C. 154(b) by 0 days.

(21) Appl. No.: 14/323,924

(22) Filed: Jul. 3, 2014

(51) Int. Cl.
  *C07C 45/63* (2006.01)
  *C07C 49/80* (2006.01)

(52) U.S. Cl.
  CPC .................. *C07C 45/63* (2013.01); *C07C 49/80* (2013.01)

(58) Field of Classification Search
  CPC ................................ C07C 49/80; C07C 45/63
  USPC ........................................................ 568/316
  See application file for complete search history.

(56) References Cited

U.S. PATENT DOCUMENTS 4,299,845 A * 11/1981 Loebenberg et al. ......... 514/599

OTHER PUBLICATIONS

Moughamir, et al., "Activation of Tetrabutylammonium Hydrogen Difluoride with Pyridine: A Mild and Efficient Procedure for Nucleophilic Fluorination," Tetrahedron Letters, 39, 1998, 7305-7306.*

Yoshino et al., "A mild ring opening fluorination of epoxide with ionic liquid 1-ethyl-3-methylimidazorium oligo hydrogefluoride (EMMIMF(HF)2.3)," Journal of Fluorine Chemistry, 125, 2004, 1127-1129.*

Akiyama et al., "Selective introduction of a fluorine atome into carbohydrates and a mucleoside by ring-opening fluorination reaction of epoxides," Journal of Fluorine Chemistry, 127, 2006, 920-923.*

* cited by examiner

*Primary Examiner* — Paul A Zucker
*Assistant Examiner* — Mark Luderer
(74) *Attorney, Agent, or Firm* — Don D. Cha; Hamilton DeSanctis & Cha, LLP

(57) ABSTRACT

The present invention provides methods and processes for producing α-fluoroalkyl ketones from non-fluoro α-haloalkyl ketones using a fluorohydrogenate compound. In some embodiments, the fluorohydrogenate compound is an ionic liquid. One particular method of the invention utilizes a fluorohydrogenate ionic liquid compound of the formula: $Q^+[F.(HF)_n]$, wherein $Q^+$ is an onium cation and n is a number from 0 to 3.

19 Claims, No Drawings

FLUORONATION OF ALPHA-HALOALKYL KETONES

FIELD OF THE INVENTION

The present invention relates to methods and processes for producing α-fluoroalkyl ketones from non-fluoro α-haloalkyl ketones using a fluorohydrogenate compound.

BACKGROUND OF THE INVENTION

Fluorine is the element with highest electronegativity. Due to its size and unique electronic properties, fluorine quite often imparts significantly different (often beneficial) properties to organic molecules. (Kirsch, Peer. 2004, *Modern Fluoroorganic Chemistry Synthesis, Reactivity, Applications*. Weinheim Wiley-VCH). It is widely known that the incorporation of fluorine into organic molecule has a significant effect on its physical, chemical, and biological properties (Welch, J. T. *Tetrahedron* 1987, 43, 3123). These changes in properties make them suitable for diverse applications in material science, agrochemistry, as well as in pharmaceutical industry (Robert Millar, Rituparna Saha, *Future Medicinal Chemistry*, 2009, 1(5) 777-779).

The α-fluoromethyl aryl ketones are often found in bioactive molecules or are often used as building blocks for other organofluorine compounds. For example, it has been well recognized that the electron withdrawing effect of fluorine atom can increase the susceptibility of the carbonyl group to hydration. In fact, this property has been exploited in the design of inhibitors of hydrolytic enzyme. See, for example, M. R. Heinrich, *Tetrahedron Lett.* 48 (2007), 3895-3908; R. Katoch-Rouse et al., *J. Med. Chem.*, 46 (2003), 642-645; B. Zajc et al., *J. Org. Chem.*, 55 (1990), 1099-1102; D. Schirlin et al., *Med. Chem. Lett.*, 3 (1993), 253-258. Due to their importance, efficient and practical synthetic strategies towards α-fluoromethyl aryl ketones have long been pursued.

In general, there are mainly two synthetic approaches to α-fluoromethyl aryl ketones. T. Furuya et al., *Curr. Opin. Drug Discovery Development*, 11 (2008), 803-819. The first approach involves the introduction of fluorine atom into non-fluorinated substrate with electrophilic fluorinating reagents, such as N-fluorosulfonimides or Selectfluor. See, for example, W. E. Barnette, *J. Am. Chem. Soc.* 106 (1984), 452-454; P. Kwiatkowski et al., *J. Am. Chem. Soc.*, 133 (2011) 1738-1741; N. Ahlsten et al., *Synthesis*, (2011) 2600-2608; E. Fuglseth et al., *Tetrahedron*, 64 (2008), 7318-7323; S. Stavber et al., *Chem. Commun.*, (2000), 1323-1324; W. Peng et al., *J. Org. Chem.*, 70 (2005), 5760-5763; T. H. K. Thvedt et al., *Tetrahedron*, 65 (2009) 9550-9556. Unfortunately, these reagents are highly expensive for use in a large scale reaction and/or are difficult to prepare due to the need for the elemental fluorine. The second approach towards α-flurormethyl aryl ketone is the nucleophilic substitution of α-bromomethyl aryl ketones with fluorine using KF/Ph₃SnF. See, for example, M. Makosza et al., *Tetrahedron Lett.*, 45 (2004), 1385-1386; KF/18-crown-6 (C. L. Liotta et al., *J. Am. Chem. Soc.*, 96 (1974), 2250-2252; L. Fitjer, *Synthesis*, 3 (1977) 189-191; KF/PEG-1000 (J. Leroy, *J. Org. Chem.*, 46 (1981), 206-209); KF/PEG-400 or TBAF:3H₂O, and ZnF₂/KF (Z. Z. Chen et al., *J. Fluorine Chem.*, 131 (2010), 340-344). However, these combinations of fluorinating reagents have low solubility, thereby limiting their usefulness in a large scale or continuous processes.

Hydrogen fluoride is the most basic nucleophilic fluorinating reagent. A. Bowers et al., *J. Am. Chem. Soc.*, 1960, 82, 4001-4007; A. Bowers et al., *J. Am. Chem. Soc.*, 1960, 82, 4007-4012. Unfortunately, due to difficulties associated with handling hydrogen fluoride, its general applicability as a fluorinating agent is severely limited. Other fluorinating reagents include pyridinium poly(hydrogen fluoride) (i.e., Py.nHF, where n is in the range from 1-10) (G. A. Olah et al., *J. Org. Chem*, 1979, 44, 3842-3881; D. Y. Chi et al., *J. Org. Chem.*, 1987, 52, 658-664) and triethylamine trihydrogen fluoride (Et₃N—3HF) (G. Alyemhe et al., *Synthesis*, 1987, 562-564; M. Tamura et al., *Synthesis*, 1995, 515-517). However, these reagents also require careful handling as they fume in air.

Therefore, there is a need for relatively safe and/or non-fuming fluorinating reagent to produce α-fluoromethyl aryl ketones.

SUMMARY OF THE INVENTION

Ionic liquids have attracted much attention as reaction media because of their low volatility, especially in the field of green and combinatorial chemistry. C. C. Tzchucke et al., *Angew. Chem. Int. Ed.*, 2002, 41, 3964-4000. Some aspects of the invention are based on the discovery by the present inventors that fluorohydrogenate ionic liquids are stable to air, moisture, and glass containers and can be used as fluorinating agents. Exemplary fluorohydrogenate ionic liquids of the invention include, but are not limited to, N-methyl-N-propylpyrrolidinium fluorohydrogenate ("Pyr₁₃F·(HF)ₙ"), N-methyl-N-butylpyrrolidinium fluorohydrogenate ("Pyr₁₄F·(HF)ₙ"), and N-methyl-N-ethylimidazolium fluorohydrogenate ("EMIMF·(HF)ₙ"), where n is a number from 0 to 3, typically 0<n≤3. In some particular embodiments, 2≤n≤3, and often n is 2.3.

One particular aspect of the invention provides a method for producing an α-fluoroalkyl aryl ketone of the formula:

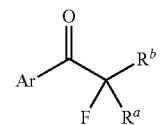

I by contacting a non-fluoro α-haloalkyl aryl ketone of the formula:

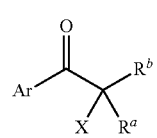

II with a fluorohydrogenate salt under reaction conditions sufficient to produce the α-fluoroalkyl ketone of the Formula I. In compounds of Formulas I and II, Ar is aryl or heteroaryl, each of which is optionally substituted; X is a non-fluoro halide; each of $R^a$ and $R^b$ is independently hydrogen, alkyl or halide; provided when $R^a$, $R^b$ or both of the non-fluoro α-haloalkyl ketone of Formula II is a non-fluoro halide, then the corresponding $R^a$, $R^b$ or both of α-halofluoroalkyl ketone of Formula I can also be fluoride. Replacement of non-fluoro halides of $R^a$ and/or $R^b$ depends on the reaction conditions such as the amount of fluorohydrogenate salt used, reaction time, reaction temperature, etc. In some instances, the method of the invention produces α-perfluoroalkyl ketone, i.e., where all of the halides α to the carbonyl carbon are replaced with fluoride. For example, when $R^a$ and $R^b$ are non-fluoro halides, the resulting product is α-trifluoromethyl aryl ketone.

In one embodiment, when a fluorohydrogenate ionic liquid is used as the fluorinating agent, it can also serve as the solvent. In other embodiments, the reaction is conducted in an organic solvent. Suitable organic solvents include, but are not limited to, dichloromethane, chloroform, tetrahydrofuran, ether, toluene, xylene, benzene, mono-, di- or tri-glyme, or a combination thereof.

In one particular embodiment, Ar is optionally substituted aryl. In some instances within this embodiment, Ar is substituted with one or more substituents, each of which is independently selected from the group consisting of $C_{1-12}$ alkyl, $C_{1-12}$ alkoxy, aryloxy, halide, cyano, and nitro. Still in other instances, Ar is substituted with one substituent selected from the group consisting of $C_{1-12}$ alkyl, $C_{1-12}$ alkoxy, aryloxy, halide, cyano, and nitro.

Yet in other embodiments, said fluorohydrogenate salt is of the formula: $Q^+[F\cdot(HF)_n]$, wherein $Q^+$ is an onium cation and n is a number from 0 to 3. Typically, $0 \leq n \leq 3$; often $1 \leq n \leq 3$, more often $2 \leq n \leq 3$.

Still in other embodiments, $Q^+$ is a quaternary ammonium cation. Within these embodiments, in some instances $Q^+$ is selected from the group consisting of N-ethyl-N-methylimidazolium, N-methyl-N-propylpyrrolidinium or N-methyl-N-butylpyrrolidinium, and a combination thereof.

In other embodiments, said fluorohydrogenate salt is an ionic liquid.

Still yet in other embodiments, $R^a$ and $R^b$ are hydrogen.

The amount of the fluorohydrogenate salt used is typically from about 1 to about 3 equivalents relative to the amount of the non-fluoro α-haloalkyl ketone of Formula II. However, it should be appreciated that the scope of the invention is not limited to any particular amount of the fluorohydrogenate salt used. In general, any amount sufficient to produce the desired α-fluoroalkyl ketone in a satisfactory yield can be used. Such amount can depend on the reaction conditions such as, but not limited to, reaction time, reaction temperature, organic solvent, reactivity of the non-fluoro α-haloalkyl ketone etc.

Yet still in other embodiments, the method of invention further comprises the steps of contacting the reaction mixture with an acidic aqueous solution. This is typical done as a work-up step to quench the reaction and/or to aid in isolation of the product. In some instances, the acidic aqueous solution comprises hydrochloric acid, aqueous HF, sulfuric acid, nitric acid, or any water soluble Lewis acid. Exemplary water soluble Lewis acids include, but are not limited to, $AlCl_3$, $BF_3$, $ZnCl_2$, $Yb(OTf)_3$, $Ga(OTf)_3$, $B(OH)_3$, and $Al_2(SO4)_3$.

In other embodiments, the α-fluoroalkyl aryl ketone product is an α-perfluoromethyl aryl ketone.

Another aspect of the invention provides a method for producing an α-fluoroalkyl aryl ketone, said method comprising contacting a non-fluoro α-haloalkyl aryl ketone with a fluorohydrogenate ionic liquid under reaction conditions sufficient to produce an α-fluoroalkyl aryl ketone.

In some embodiments, the α-fluoroalkyl aryl ketone is α-fluoromethyl aryl ketone.

Still in other embodiments within this aspect of the invention, the fluorohydrogenate ionic liquid comprises N-methyl-N-propylpyrrolidinium fluorohydrogenate, N-methyl-N-butylpyrrolidinium fluorohydrogenate, N-methyl-N-ethylimidazolium fluorohydrogenate or a mixture thereof.

DETAILED DESCRIPTION OF THE INVENTION

Definitions

"Alkyl" refers to a saturated linear monovalent hydrocarbon moiety, typically of one to twelve, often one to six, carbon atoms or a saturated branched monovalent hydrocarbon moiety, typically of three to twelve, often three to six, carbon atoms. Exemplary alkyl group include, but are not limited to, methyl, ethyl, n-propyl, 2-propyl, tert-butyl, pentyl, and the like.

"Aryl" refers to a monovalent mono-, bi- or tricyclic aromatic hydrocarbon moiety of 6 to 15 ring atoms which is optionally substituted with one or more substituents. When the aryl group is substituted, it is typically substituted with one, two, or three substituents, often one substituent, within the ring structure. When two or more substituents are present in an aryl group, each substituent is independently selected. Exemplary substituents of aryl group include, but are not limited to, alkyl, halo, haloalkyl, cyano, nitro, amino, monoalkyl amino, dialkylamino, —$OR^a$ (where $R^a$ is hydrogen or alkyl), etc. Exemplary aryl groups include, but are not limited to, phenyl, naphthyl, anthrancenyl, phenanthryl, etc.

The term "non-fluoro α-haloalkyl aryl ketone" refers to a ketone in which the halide on the alkyl group is not fluoride. Thus, the halogen group that is attached to the alkyl group can be chloro, bromo, or iodo.

The term "fluorohydrogenate salt" refers to an ionic compound having a fluorohydrogenate anion. Typically, fluorohydrogenate anion is written as $F^-\cdot(HF)n$ or $F^-\cdot n(HF)$, where n is a number as disclosed herein. This formula represents hydrogen fluoride solvated fluoride anion, i.e., the variable n represents the molar equivalent of hydrogen fluoride that is present per mole of fluoride ion. Typically, the fluoride anion is solvated with one or more, typically two or three hydrogen fluoride moieties.

The term "fluorohydrogenate ionic liquid" refers to an ionic liquid comprising one or more fluorohydrogenate anions. Hydrogen fluoride is highly soluble in some fluorohydrogenate ionic liquids, and the empirical stoichiometry of HF relative to the fluoride anion can vary from 0 to 3 as discussed above, i.e., fluorohydrogenate anion can be from and $F^-\cdot 3HF$ (which can alternatively be expressed as $F^-\cdot(HF)_3$). Thus, HF stoichiometry n in the empirical anion formula $F^-\cdot nHF$ (i.e., $F^-\cdot(HF)_n$) can be between 0 and 3, inclusive. Typically, fluorohydrogenate ionic liquids have melting points below 100° C. and are often a liquid at room temperature. Some fluorohydrogenate ionic liquids are vacuum-stable and have an empirical formula $F^-\cdot 2.3HF$ (i.e., $F^-\cdot(HF)_{2.3}$). The fluorohydrogenate ionic liquid also includes a counter cation. Typically, the counter cation is a quaternary ammonium cation. The counter cation may also be a phosphonium or thiazolium cation. Often, the quaternary ammonium cation comprises a nitrogen-heteroaryl cation. Exemplary vacuum stable fluorohydrogenate ionic liquids include, but are not limited to, N-methyl-N-butylpyrrolidinium fluorohydrogenate ("$PYR_{14}F\cdot(HF)_{2.3}$"), N-methyl-N-propylpyrrolidinium fluorohydrogenate ("$PYR_{13}F\cdot(HF)_{2.3}$"), and N-ethyl-N-methylimidazolium fluorohydrogenate ("$EMIMF\cdot(HF)_{2.3}$").

The terms "halo," "halogen" and "halide" are used interchangeably herein and refer to fluoro, chloro, bromo, or iodo.

The terms "non-fluoro halo" and "non-fluoro halide" are used interchangeably herein and refer to a halide as defined herein but excludes fluoro group. Thus, "non-fluoro halo" or "non-fluoro halide" refers to chloro, bromo or iodo.

The term "heteroaryl" means a monovalent monocyclic or bicyclic aromatic moiety of 5 to 12 ring atoms containing one, two, or three ring heteroatoms selected from N, 0, or S, the remaining ring atoms being C. The heteroaryl ring is optionally substituted independently with one or more substituents, typically one or two substituents, selected from the substituents discussed herein. Exemplary heteroaryl groups include, but are not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, etc.

When describing a chemical reaction, the terms "treating", "contacting" and "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow and/or narrower definitions, if any.

Methods and Processes of the Invention

Some aspects of the invention are based on the discovery by the present inventors that reacting an α-haloalkyl ketones with a fluorohydrogenate salt produces the corresponding α-fluoroalkyl ketones. One particular aspect of the reaction can be generalized by the following reaction equation:

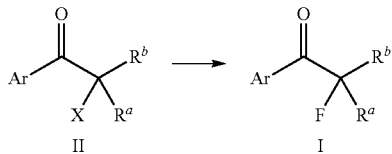

where Ar is aryl or heteroaryl, each of which is optionally substituted; X is a non-fluoro halide; each of $R^a$ and $R^b$ is independently hydrogen, alkyl or halide; provided when $R^a$, $R^b$ or both of the non-fluoro α-haloalkyl ketone of Formula II is a non-fluoro halide, then the corresponding $R^a$, $R^b$ or both of α-halofluoroalkyl ketone of Formula I can also be fluoride. Thus, in general the method of the invention replaces at least one of the non-halide group(s) in the non-fluoro α-haloalkyl ketone of Formula II by with fluoride group. It should be appreciated that if the non-fluoro α-haloalkyl ketone of Formula II has two or more non-fluoro α-halides total (i.e., $R^a$, $R^b$ or both are non-fluoro halides) then the α-fluorohaloalkyl ketone compound of Formula I can have up to three α-fluoro groups. The number of substitution by the fluoride group will depend on a variety of factors, including, but not limited to, the reaction time and temperature, reaction solvent, reactivity of the compound of Formula II, reactivity of the fluorohydrogenate salt, the amount of fluorohydrogenate salt used, etc. The halide substituent in α-haloalkyl ketone of Formula II can be chloro, bromo or iodo. It was discovered that a bromide substituent present at a carbon adjacent to the carbonyl group (i.e., α-bromoalkyl ketone, where the bromide is present adjacent to the carbonyl group, i.e., α-position) is particularly susceptible to replacement by fluoride using the method of invention.

As discussed above, methods for producing α-fluoromethyl aryl ketones using conventional fluorinating reagents, such as anhydrous HF, KF/Ph$_3$SnF, KF/18-crown-6, KF/PEG-1000, KF/PEG-400 or TBAF:3H$_2$O, and ZnF$_2$/KF are not commercially suitable. The method of invention overcomes many of the deficiencies of conventional methods for producing α-fluoroalkyl ketones in general, but in particular α-fluoromethyl aryl ketones, by utilizing a fluorohydrogenate salt. In some embodiments, the fluorohydrogenate salt is an ionic liquid. The method of invention is applicable to a variety of non-fluoro α-haloalkyl ketones, thereby providing a facile and simple method for producing a wide variety of α-fluoroalkyl ketones. In some embodiments, the non-fluoro α-haloalkyl ketone is a compound of Formula I.

In some embodiments, Ar is aryl or heteroaryl, each of which is optionally substituted, typically Ar is aryl which is optionally substituted. In other embodiments, X is halide selected from the group consisting of chloro, bromo and iodo. Often X is chloro or bromo, and most often X is bromo. Still in other embodiments, each of $R^a$ and $R^b$ is independently hydrogen, alkyl, or halide. Typically, each of $R^a$ and $R^b$ is independently hydrogen or $C_{1-12}$ alkyl, often hydrogen or $C_{1-6}$ alkyl, and most often hydrogen or $C_{1-4}$ alkyl. In one particular embodiment, $R^a$ and $R^b$ are hydrogen. When one or more of $R^a$ and $R^b$ in compound of Formula II is non-fluoro halides, product of the reaction, i.e., compound of Formula I, can also include substitution of one or more of such non-fluoro halide with fluoride.

When substituted, the aryl or the heteroaryl group has one to five, typically one, two or three substituents, each of which is independently selected. In general, the aryl or the heteroaryl group can have any substituent(s) that do not significantly interfere with the α-fluoronation reaction of a non-fluoro α-haloalkyl ketone. Exemplary substituents of the aryl or the heteroaryl group include, but are not limited to, alkyl (in particular $C_{1-12}$ alkyl), alkoxy (in particular $C_{1-12}$ alkoxy), halide, aryl, aryloxy, cyano (—CN) and nitro (—NO$_2$). Thus, a wide variety of non-fluoro α-haloalkyl ketone compounds can be fluorinated using the method of the invention. In some embodiments, the method of the invention is used to fluorinate a non-fluoro α-halomethyl aryl ketone compound, i.e., a compound of Formula II where $R^a$ and $R^b$ are hydrogen and Ar is optionally substituted aryl.

SCHEME 1

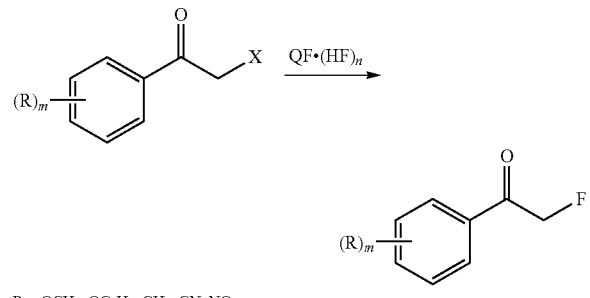

R = OCH$_3$, OC$_6$H$_5$, CH$_3$, CN, NO$_2$
m = 0-5
QF•(HF)$_n$ = PYR$_{14}$F•(HF)$_{2.3}$, PYR$_{13}$F•(HF)$_{2.3}$, EMIMF•(HF)$_{2.3}$

As illustrated in Scheme 1, one particular embodiment of the invention provides a simple, one-step process for producing α-fluoromethyl aryl ketones. The method typically includes reacting an α-halomethyl aryl ketone compound with a fluorohydrogenate ionic liquid, such as EMIMF·(HF)$_{2.3}$, PYR$_{14}$·(HF)$_{2.3}$, PYR$_{13}$—(HF)$_{2.3}$ or a combination thereof. It should be appreciated that while Scheme 1 illustrates using a fluorohydrogenate ionic liquid as the fluorinating reagent, the scope of the invention is not limited to an ionic liquid fluorohydrogenates, but in general any compound comprising a fluorohydrogenate anion can be used to fluorinate a non-fluoro α-haloalkyl ketone. A typical amount of a fluorohydrogenate compound used in processes of the invention is 1 equivalent, often about 2 equivalents or less, more often about 3 equivalent, relative to the amount of α-halomethyl aryl ketone compound.

The reaction temperature can vary depending on a variety of factors such as, but not limited to, reactivity of the α-haloalkyl ketone compound, amount and the nature of the fluorohydrogenate compound, reaction solvent, reaction time, reaction temperature, etc. A typical reaction temperature ranges from about 0° C. to about 110° C., typically from about 25° C. to about 80° C. and often from about 50° C. to about 80° C. Generally, the reaction is carried out at about 80° C.

The yield of the final product can also vary depending on a wide variety of factors such as those describe above. Typically, the yield of the product is at least 80%, often at least 90%, and more often at least 95%.

The reaction time can vary greatly depending on a variety factors such as those discussed above. In addition, the concentration of the reactants can also influence the reaction time. Typically, however, the reaction time ranges from 1 h to about 24 h, often from about 1 h to about 12, and more often from about 1 h to about 6 h.

Some aspects of the involve methods for using a fluorohydrogenate ionic liquid in a halogen exchange reaction. Thus, conversion of Cl to F, Br to F, and I to F are readily achieved in a high yield. In some instances, the reaction also produces halide by-products, which can be easily removed and recycled.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

All the reactions were carried out under anhydrous argon atmosphere. All the fluorohydrogenate ionic liquids were prepared using anhydrous HF under anhydrous conditions.

Example 1

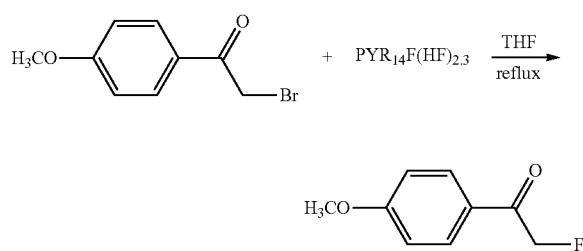

Pyr$_{14}$F·(HF)$_{2.3}$ (1.24 g, 6 mmol) was taken in a dry flask under argon atmosphere and dissolved in 10 ml of anhydrous THF. A solution of 2-bromo-1-(4-methoxyphenyl) ethanone (0.458 g, 2 mmol) in 5 ml of anhydrous THF was added slowly with syringe. The resulting reaction mixture was heated to reflux (oil bath temperature 80° C.) under stirring for 20 h. The reaction mixture was then cooled to room temperature and the solvent was removed at reduced pressure. The obtained residue was diluted with diethyl ether (20 ml) and washed with dilute HCl (0.2 M, 3×20 ml). Ethereal solution was dried over anhydrous magnesium sulfate (2 g) and filtered. Ether solution was concentrated at reduced pressure to afford a solid product. Yield: 295.6 g, 88%. Fluorine NMR in CDCl$_3$ showed a triplet at −230.05 ppm with J$_{H-F}$=47 Hz.

Example 2

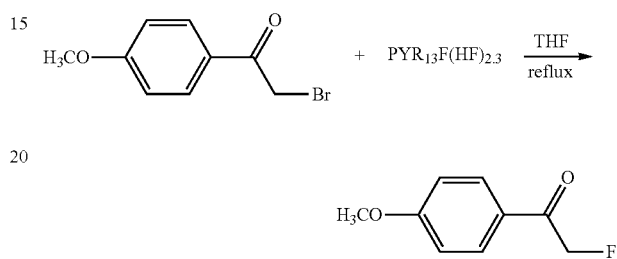

Pyr$_{13}$F·(HF)$_{2.3}$ (1.16 g, 6 mmol) was placed in a dry flask under argon atmosphere and dissolved in 10 ml of anhydrous THF. A solution of 2-bromo-1-(4-methoxyphenyl) ethanone (0.458 g, 2 mmol) in 5 ml of anhydrous THF was added slowly with syringe. The resulting mixture was heated to reflux (oil bath temperature 80° C.) under stirring for 20 h. The reaction mixture was then cooled and solvent was removed at reduced pressure. The obtained residue was diluted with diethyl ether (20 ml) and washed with dilute HCl (0.2 M, 3×20 ml). Ethereal solution was dried over anhydrous magnesium sulfate (2 g) and filtered. Ether solution was concentrated at reduced pressure to afford a solid product. Yield: 285 g, 85%.

Example 3

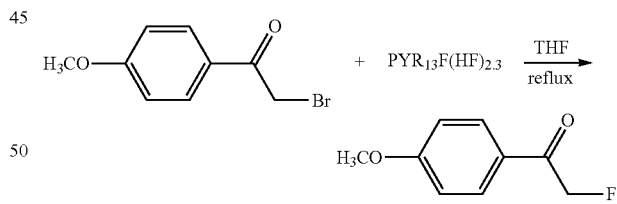

EMIMF·(HF)$_{2.3}$ (1.06 g, 6 mmol) was placed in a dry flask under argon atmosphere and dissolved in 10 ml of anhydrous THF. A solution of 2-bromo-1-(4-methoxyphenyl) ethanone (0.458 g, 2 mmol) in 5 ml of anhydrous THF was added slowly with syringe. The resulting mixture was heated to reflux (oil bath temperature 80° C.) under stirring for 20 h. The reaction mixture was then cooled to room temperature and the solvent was removed at reduced pressure. The residue was diluted with diethyl ether (20 ml) and washed with dilute HCl (0.2 M, 3×20 ml). Ethereal solution was dried over anhydrous magnesium sulfate (2 g) and filtered. Ether solution was concentrated at reduced pressure to afford a solid product. Yield: 290 g, 86%.

Example 4

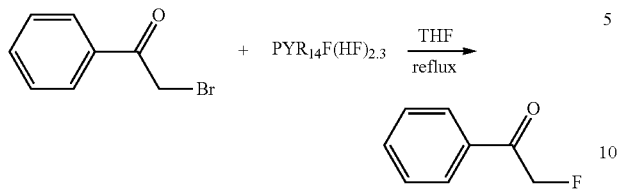

Pyr$_{14}$F·(HF)$_{2.3}$ (1.86 g, 9 mmol) was placed in a dry flask under argon atmosphere and dissolved in 15 ml of anhydrous THF. A solution of 2-bromo-1-phenyl ethanone (0.597 g, 3 mmol) in 5 ml of anhydrous THF was added slowly with syringe. The resulting mixture was heated to reflux (oil bath temperature 80° C.) with stirring for 20 h. The reaction mixture was then cooled to room temperature and solvent was removed at reduced pressure. The residue was diluted with diethyl ether (25 ml) and washed with dilute HCl (0.2 M, 3×25 ml). Ethereal solution was dried over anhydrous magnesium sulfate (2 g) and filtered. Ether solution was concentrated at reduced pressure to afford a liquid product. Yield: 372 g, 90%.

Example 5

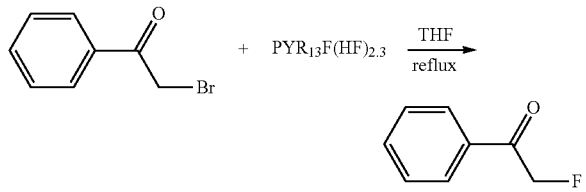

Pyr$_{13}$F·(HF)$_{2.3}$ (1.15 g, 6 mmol) was placed in a dry flask under argon atmosphere and dissolved in 10 ml of anhydrous THF. A solution of 2-bromo-1-phenyl ethanone (0.496 g, 2.5 mmol) in 5 ml of anhydrous THF was added slowly with syringe. The resulting mixture was heated to reflux (oil bath temperature 80° C.) with stirring for 20 h. The reaction mixture was then cooled to room temperature and the solvent was removed at reduced pressure. The residue was diluted with diethyl ether (20 ml) and washed with dilute HCl (0.2 M, 3×20 ml). Ethereal solution was dried over anhydrous magnesium sulfate (2 g) and filtered. Ether solution was concentrated at reduced pressure to afford a liquid product. Yield: 240 g, 87%.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for producing an α-fluoroalkyl ketone of the formula:

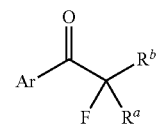

I said method consisting essentially of contacting a non-fluoro α-haloalkyl ketone of the formula:

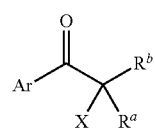

II with a fluorohydrogenate salt under reaction conditions sufficient to produce an α-fluoroalkyl ketone of the Formula I, wherein the fluoride anion of said fluorohydrogenate salt is solvated with >1 and ≤3 equivalent of hydrogen fluoride, and wherein Ar is aryl or heteroaryl, each of which is optionally substituted;

X is a non-fluoro halide;

each of $R^a$ and $R^b$ is independently hydrogen, alkyl or halide;

provided when $R^a$, $R^b$ or both of the non-fluoro α-haloalkyl ketone of Formula II is a non-fluoro halide, then the corresponding $R^a$, $R^b$ or both of α-halofluoroalkyl ketone of Formula I that is produced can also be fluoride.

2. The method of claim 1, wherein Ar is optionally substituted aryl.

3. The method of claim 2, wherein Ar is substituted with one or more substituents, each of which is independently selected from the group consisting of $C_{1-12}$ alkyl, $C_{1-12}$ alkoxy, aryloxy, halide, cyano, and nitro.

4. The method of claim 1, wherein said fluorohydrogenate salt is of the formula: $Q^+[F \cdot (HF)_n]$, wherein Q is an onium cation and 1<n≤3.

5. The method of claim 4, wherein $Q^+$ is a quaternary ammonium cation, a quaternary phosphonium cation or a quaternary thiazolium cation.

6. The method of claim 5, wherein $Q^+$ is a quaternary ammonium cation.

7. The method of claim 6, wherein $Q^+$ is selected from the group consisting of N-ethyl-N-methylimidazolium, N-methyl-N-propylpyrrolidinium or N-methyl-N-butylpyrrolidinium, and a combination thereof.

8. The method of claim 1, wherein said fluorohydrogenate salt is an ionic liquid.

9. The method of claim 1, wherein $R^a$ and $R^b$ are hydrogen.

10. The method of claim 1, wherein the reaction is carried out in the presence of an organic solvent.

11. The method of claim 10, wherein the organic solvent comprises dichloromethane, chloroform, tetrahydrofuran, ether, toluene, mono-, di- or triglyme, or a combination thereof.

12. The method of claim 1, wherein the amount of said fluorohydrogenate salt used is from about 1 to about 3 equivalents relative to the amount of said non-fluoro α-halomethyl aryl ketones.

13. The method of claim 1 further comprising the steps of contacting the reaction mixture with an acidic aqueous solution.

14. The method of claim 13, wherein said acidic aqueous solution comprises hydrochloric acid, aqueous HF, sulfuric acid, nitric acid, or any water soluble Lewis acid.

15. The method of claim 1, wherein said α-fluoromethyl aryl ketone is an α-perfluoromethyl aryl ketone.

16. A method for producing an α-fluoroalkyl aryl ketone, said method consisting essentially of contacting a non-fluoro α-haloalkyl aryl ketone with a fluorohydrogenate ionic liquid optionally in the presence of a solvent under reaction conditions sufficient to produce an α-fluoroalkyl aryl ketone.

17. The method of claim 16, wherein said α-fluoroalkyl aryl ketone is α-fluoromethyl aryl ketone.

18. The method of claim 16, wherein said fluorohydrogenate ionic liquid comprises N-methyl-N-propylpyrrolidinium fluorohydrogenate, N-methyl-N-butylpyrrolidinium fluorohydrogenate, N-methyl-N-ethylimidazolium fluorohydrogenate or a mixture thereof.

19. A method for producing an α-perfluoroalkyl ketone of the formula:

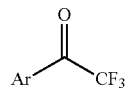

said method comprising contacting a non-fluoro α-haloalkyl ketone of the formula:

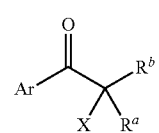

with a fluorohydrogenate salt under reaction conditions sufficient to produce an α-fluoroalkyl ketone of the Formula I, wherein
  Ar is aryl or heteroaryl, each of which is optionally substituted;
  X is a non-fluoro halide; and
  each of $R^a$ and $R^b$ is independently a halide.

* * * * *